United States Patent
Erdtmann

(10) Patent No.: US 9,915,609 B1
(45) Date of Patent: Mar. 13, 2018

(54) SYSTEM AND METHOD OF SMOKE DETECTION USING MULTIPLE WAVELENGTHS OF LIGHT

(71) Applicant: Matthew Erdtmann, Londonderry, NH (US)

(72) Inventor: Matthew Erdtmann, Londonderry, NH (US)

(73) Assignee: VALOR FIRE SAFETY, LLC, Londonderry, NH (US)

( * ) Notice: Subject to any disclaimer, the term of this patent is extended or adjusted under 35 U.S.C. 154(b) by 48 days.

(21) Appl. No.: 15/207,646

(22) Filed: Jul. 12, 2016

Related U.S. Application Data

(63) Continuation-in-part of application No. 14/821,155, filed on Aug. 7, 2015, now Pat. No. 9,482,607, which is a continuation of application No. 14/522,971, filed on Oct. 24, 2014, now Pat. No. 9,140,646, which is a continuation-in-part of application No. 14/067,431, filed on Oct. 30, 2013, now Pat. No. 8,907,802, which is a continuation-in-part of application No. 13/799,816, filed on Mar. 13, 2013, now Pat. No. 8,947,243, and a continuation-in-part of application No. 13/799,826, filed on Mar. 13, 2013, now Pat. No. 8,952,821, and a continuation-in-part of application No. 13/800,071, filed on Mar. 13, 2013, now Pat. No. 8,947,244.

(60) Provisional application No. 62/191,668, filed on Jul. 13, 2015, provisional application No. 62/202,974, filed on Aug. 10, 2015, provisional application No. 61/639,935, filed on Apr. 29, 2012.

(51) Int. Cl.
*G08B 21/00* (2006.01)
*G01N 21/53* (2006.01)

(52) U.S. Cl.
CPC ....... *G01N 21/53* (2013.01); *G01N 2201/062* (2013.01); *G01N 2201/12* (2013.01)

(58) Field of Classification Search
CPC .............................. G08B 17/103; G01N 21/53
USPC ..... 340/515, 628, 629, 630, 693.5; 250/574, 250/575; 356/437, 438, 439
See application file for complete search history.

(56) References Cited

U.S. PATENT DOCUMENTS

2011/0221889 A1* 9/2011 Knox ..................... G01N 21/53 348/135

* cited by examiner

*Primary Examiner* — Jeffery Hofsass
(74) *Attorney, Agent, or Firm* — Morgan, Lewis & Bockius LLP

(57) ABSTRACT

In accordance with certain embodiments, detection of a fire event via detection of scattered light of at least two wavelengths is based on rates of change between measurements of the scattered light of the different wavelengths.

13 Claims, 6 Drawing Sheets

SYSTEM AND METHOD OF SMOKE DETECTION USING MULTIPLE WAVELENGTHS OF LIGHT

RELATED APPLICATIONS

This application claims the benefit of and priority to U.S. Provisional Patent Application No. 62/191,668, filed Jul. 13, 2015, and U.S. Provisional Patent Application No. 62/202,974, filed Aug. 10, 2015, the entire disclosure of each of which is hereby incorporated herein by reference. This application is also a continuation-in-part of U.S. patent application Ser. No. 14/821,155, filed Aug. 7, 2015, which is a continuation of U.S. patent application Ser. No. 14/522,971, filed on Oct. 24, 2014, which a continuation-in-part of U.S. patent application Ser. No. 14/067,431, filed Oct. 30, 2013, which is (a) a continuation-in-part of U.S. patent application Ser. No. 13/799,816, filed Mar. 13, 2013, which claims the benefit of and priority to U.S. Provisional Patent Application No. 61/639,935, filed Apr. 29, 2012, (b) a continuation-in-part of U.S. patent application Ser. No. 13/799,826, filed Mar. 13, 2013, which claims the benefit of and priority to U.S. Provisional Patent Application No. 61/639,935, filed Apr. 29, 2012, and (c) a continuation-in-part of U.S. patent application Ser. No. 13/800,071, filed Mar. 13, 2013, which claims the benefit of and priority to U.S. Provisional Patent Application No. 61/639,935, filed Apr. 29, 2012. The entire disclosure of each of these applications is hereby incorporated herein by reference.

FIELD OF THE INVENTION

In various embodiments, the present invention relates to smoke detection systems and methods utilizing multiple wavelengths of light.

BACKGROUND

The ultimate goal of a smoke detector is to quickly detect every fire event and ignore every nuisance event. Virtually all smoke detectors manufactured today fall short of this goal, either because they are slow to activate during certain fire events or unwittingly activate during certain nuisance events. The primary reason is that a fire event produces several distinct signatures, including smoke, light, heat, humidity, certain gases, and sound, but most smoke detectors are designed to detect only one signature, smoke. Conventional smoke detectors thus generally cannot discriminate between smoke particles and certain nuisance particles, such as dust, steam, or cooking aerosols. This typically forces the smoke detectors to be either insufficiently sensitive, activating very slowly in response to smoke particles, or overly sensitive, activating very quickly (and erroneously) in response to nuisance particles.

Photoelectric smoke detectors operate by illuminating a sampling volume with light from a light emitter and detecting light scattered by any particles in the sampling volume with a light receiver. One technique for photoelectric smoke detectors to better discriminate between smoke particles and nuisance particles is to use two different wavelengths of light. Smoke particles are generally smaller than nuisance particles and will scatter light more efficiently than nuisance particles as the wavelength decreases. Thus, by evaluating the scattering of light by two wavelengths, smoke particles may generally be discriminated from nuisance particles.

While this technique helps to discriminate between smoke particles and nuisance particles, it may not necessarily decrease the time to activate, since smoke still must travel from the fire source to the smoke detector, and, if the sampling volume is located inside the smoke detector, the smoke must also enter the smoke detector and any detection chamber contained therein. Thus, there is a need for smoke detectors with more rapid response times and that reliably distinguish between fire events and nuisance events.

SUMMARY

In accordance with various embodiments of the present invention, to better discriminate fire events from nuisance events, and decrease the time to activate, additional sensors responsive to fire signatures other than smoke are incorporated in or on the smoke detector. These may include, but are not limited to, sensors for light, heat, humidity, gases, proximity, and sound. By identifying additional signatures of the fire, the additional sensors enable the smoke detector to more reliably discriminate fire events from nuisance events. Also, since information carried by the additional signatures of the fire may travel more quickly to the smoke detector than the smoke itself, the additional sensors may decrease the time to activate since the smoke detector becomes aware of the fire event sooner. For example, the light emitted by a flaming fire will travel to the smoke detector almost instantly, whereas smoke may take seconds or minutes to travel to the smoke detector. Having a few extra seconds available to escape a fire may make the difference between life and death.

Thus, in accordance with various embodiments of the present invention, a smoke detector uses at least two wavelengths of light to detect smoke via light scattering and at least one additional sensor to detect at least one fire signature other than smoke. In accordance with various other embodiments, a smoke detector uses at least two wavelengths of light to detect smoke via light scattering and a timer to measure a rate of increase of the smoke. In accordance with embodiments of the invention, better discrimination between fire events and nuisance events and decreased activation time are achieved. Measurements taken via one or more light receivers and/or other sensors may be acquired over multiple measurement cycles. In various embodiments, a single measurement cycle corresponds to the time between measurements acquired by one or more receivers and/or sensors when in a continuous or periodic monitoring mode.

Embodiments of the invention also distinguish between smoke particles and nuisance particles based at least in part on specific interactions between such particles and multiple different wavelengths of light. (As utilized herein, "nuisance particles" broadly refers to vapors or airborne particulates not originating from a fire and that typically have average diameters larger (e.g., at least ten times larger and/or at least one micron in diameter) than typical smoke particles. Non-limiting examples of nuisance particles are steam, cooking aerosols (e.g., vegetable oil, toast, hamburger, bacon, etc.), powder, and dust (e.g., cement dust).) Because nuisance particles typically are larger than smoke particles, they will tend to scatter light of various wavelengths differently. Thus, discrimination between smoke particles and nuisance particles may be achieved by generating multiple signals each using distinct wavelengths of light. Airborne particles other than smoke, such as dust, powders, cooking aerosols, or water vapor, scatter the various wavelengths of light throughout the near ultraviolet, visible, and near infrared (e.g., wavelengths of approximately 300-1000 nm) generally equally because these particles have a diameter on the order of several microns. However, smoke particles, which typically have a diameter of less than one micron, typically scatter the shorter wavelengths of light much more strongly than the longer wavelengths. By using multiple light emitters, at least one with a shorter emission wavelength, such as green, blue, violet, or ultraviolet (e.g., wavelengths of approximately 300-570 nm), and at least one with a longer emission wavelength, such as red or infrared (e.g., wavelengths of approximately 630-1000 nm), the relative signals may be compared to determine whether the airborne particles within the sampling volume are smoke particles or not. As known to those of skill in the art, light emitters such as light-emitting diodes (LEDs) and lasers that emit at particular wavelengths may be produced by, e.g., selection and/or adjustment of the band gap and/or lasing cavity size of a semiconductor-based light emitter.

In an aspect, embodiments of the invention feature a method of smoke detection that may utilize a smoke detector comprising (a) a housing, (b) one or more light emitters, and (c) one or more light detectors. In a step (A), a first measurement of light including a first wavelength is acquired from a sampling volume while emitting light of approximately the first wavelength with at least one light emitter, and the first measurement is compared to a first threshold. In a step (B), a measurement of a fire signature other than smoke is acquired, and the measurement of the fire signature other than smoke is compared to a second threshold. Only one of steps (A) or (B) may be performed, or both steps (A) and (B) may be performed. If both steps (A) and (B) are performed, steps (A) and (B) may be performed sequentially, or at least portions (i.e., portions or the entireties) of steps (A) and (B) may be performed simultaneously. If the first threshold and/or the second threshold is exceeded, the steps (C), (D), and (E) are performed. In step (C), a second measurement of light including a second wavelength is acquired from the sampling volume while emitting light of approximately the second wavelength with at least one light emitter. In step (D), a third measurement of light including a third wavelength is acquired from the sampling volume while emitting light of approximately the third wavelength with at least one light emitter, the third wavelength being longer than the second wavelength. In step (E), the presence of smoke particles within the sampling volume is determined based on the second measurement of light and the third measurement of light.

Embodiments of the invention may include one or more of the following in any of a variety of combinations. An ambient light level outside of the housing may be detected. The second measurement of light may be corrected based at least in part on the detected ambient light level, thereby producing a corrected second-wavelength measurement. The third measurement of light may be corrected based at least in part on the detected ambient light level, thereby producing a corrected third-wavelength measurement. The presence of smoke particles within the sampling volume may be determined based on the corrected second-wavelength measurement and the corrected third wavelength measurement (e.g., a sum of, a ratio of, or a difference between the corrected second-wavelength measurement and the corrected third wavelength measurement). The first wavelength may be approximately equal to the second wavelength or the third wavelength. The first wavelength may be different from the second wavelength and the third wavelength. The fire signature other than smoke may include, consist essentially of, or consist of light, light flicker, heat, sound, moisture, a gaseous combustion byproduct, and/or an airborne effluent. The sampling volume may be disposed inside and/or outside of the housing. Determining the presence of smoke particles within the sampling volume may include, consist essentially of, or consist of comparing, to a threshold, (i) the second measurement, (ii) the third measurement, (iii) a sum of the second and third measurements, (iv) a difference between the second measurement and the third measurement, and/or (v) a ratio of the second and third measurements. The second wavelength may range from approximately 200 nm to approximately 700 nm. The third wavelength may range from approximately 700 nm to approximately 1100 nm.

At least a portion of the second measurement may be acquired while emitting light of approximately the third wavelength with at least one light emitter. At least a portion of the third measurement may be acquired while emitting light of approximately the second wavelength with at least one light emitter. Steps (C), (D), and (E) may be performed only if both the first threshold and the second threshold are exceeded. The fire signature other than smoke may include, consist essentially of, or consist of light flicker. The second threshold being exceeded may include, consist essentially of, or consist of the light flicker having a frequency ranging from approximately 1 Hz to approximately 20 Hz. Both steps (A) and (B) may be performed. Steps (C) and (D) may be performed sequentially. Portions, or substantially all, of steps (C) and (D) may be performed simultaneously.

In another aspect, embodiments of the invention feature a method of smoke detection that may utilize a smoke detector comprising (a) a housing, (b) one or more light emitters, and (c) one or more light detectors. In a step (A), a first measurement of light including a first wavelength is acquired from a sampling volume while emitting light of approximately the first wavelength with at least one light emitter, and the first measurement is compared to a first threshold. In a step (B), a measurement of a fire signature other than smoke is acquired, and the measurement of the fire signature other than smoke is compared to a second threshold. Only one of steps (A) or (B) may be performed, or both steps (A) and (B) may be performed. If both steps (A) and (B) are performed, steps (A) and (B) may be performed sequentially, or at least portions (i.e., portions or the entireties) of steps (A) and (B) may be performed simultaneously. If the first threshold and/or the second threshold is exceeded, the steps (C) and (D) are performed. In step (C), a second measurement of light including (i) a second wavelength and (ii) a third wavelength longer than the second wavelength is acquired from the sampling volume while emitting light of approximately the second and third wavelengths with at least one light emitter. In step (D), the presence of smoke particles within the sampling volume is determined based on the second measurement of light.

Embodiments of the invention may include one or more of the following in any of a variety of combinations. An ambient light level outside of the housing may be detected. The second measurement of light may be corrected based at least in part on the detected ambient light level, thereby producing a corrected second-wavelength measurement. The presence of smoke particles within the sampling volume may be determined based on the corrected second-wavelength measurement. The first wavelength may be approximately equal to the second wavelength or the third wavelength. The first wavelength may be different from the second wavelength and the third wavelength. The fire signature other than smoke may include, consist essentially of, or consist of light, light flicker, heat, sound, moisture, a gaseous combustion byproduct, and/or an airborne effluent. The sampling volume may be disposed inside and/or outside of the housing. Determining the presence of smoke particles within the sampling volume may include, consist essentially of, or consist of comparing the second measurement to a threshold. Steps (C) and (D) may be performed only if both the first threshold and the second threshold are exceeded. The fire signature other than smoke may include, consist essentially of, or consist of light flicker. The second threshold being exceeded may include, consist essentially of, or consist of the light flicker having a frequency ranging from approximately 1 Hz to approximately 20 Hz. Both steps (A) and (B) may be performed.

In yet another aspect, embodiments of the invention feature a method of smoke detection that may utilize a smoke detector comprising (a) a housing, (b) one or more light emitters, and (c) one or more light detectors. During a first time period, (i) a first measurement of light including a first wavelength is acquired from a sampling volume while emitting light of approximately the first wavelength with at least one light emitter, and (ii) a second measurement of light including a second wavelength longer than the first wavelength is acquired from the sampling volume while emitting light of approximately the second wavelength with at least one light emitter. During a second time period later than the first time period by an elapsed time, (i) a third measurement of light including the first wavelength is acquired from the sampling volume while emitting light of approximately the first wavelength with at least one light emitter, and (ii) a fourth measurement of light including the second wavelength is acquired from the sampling volume while emitting light of approximately the second wavelength with at least one light emitter. The presence of smoke particles within the sampling volume is determined based on at least two of the first, second, third, or fourth measurements (e.g., (i) a rate of change between the first and third measurements, and/or (ii) a rate of change between the second and fourth measurements).

Embodiments of the invention may include one or more of the following in any of a variety of combinations. Determining the presence of smoke particles within the sampling volume may include, consist essentially of, or consist of (i) comparing to a threshold a difference between the first and third measurements divided by the elapsed time, and/or (ii) comparing to a threshold a difference between the second and fourth measurements divided by the elapsed time. At least a portion of the second measurement may be acquired while emitting light of approximately the first wavelength with at least one light emitter. No portion of the second measurement may be acquired while emitting light of approximately the first wavelength with at least one light emitter. At least a portion of the first measurement may be acquired while emitting light of approximately the second wavelength with at least one light emitter. No portion of the first measurement may be acquired while emitting light of approximately the second wavelength with at least one light emitter. At least a portion of the fourth measurement may be acquired while emitting light of approximately the first wavelength with at least one light emitter. No portion of the fourth measurement may be acquired while emitting light of approximately the first wavelength with at least one light emitter. At least a portion of the third measurement may be acquired while emitting light of approximately the second wavelength with at least one said light emitter. No portion of the third measurement may be acquired while emitting light of approximately the second wavelength with at least one said light emitter. The sampling volume may be disposed inside and/or outside of the housing. The presence of smoke particles within the sampling volume may be determined based on both (i) the rate of change between the first and third measurements, and (ii) the rate of change between the second and fourth measurements.

In another aspect, embodiments of the invention feature a method of smoke detection that may utilize a smoke detector comprising (a) a housing, (b) one or more light emitters, and (c) one or more light detectors. During a first time period, a first measurement of light including (i) a first wavelength and (ii) a second wavelength longer than the first wavelength is acquired from a sampling volume while emitting light of approximately the first and second wavelengths with at least one light emitter. During a second time period later than the first time period by an elapsed time, a second measurement of light including the first and second wavelengths is acquired from the sampling volume while emitting light of approximately the first and second wavelengths with at least one light emitter. The presence of smoke particles within the sampling volume is determined based on the first and second measurements (e.g., a rate of change between the first and second measurements).

Embodiments of the invention may include one or more of the following in any of a variety of combinations. Determining the presence of smoke particles within the sampling volume may include, consist essentially of, or consist of comparing to a threshold a difference between the first and second measurements divided by the elapsed time. The sampling volume may be disposed inside and/or outside of the housing.

In yet another aspect, embodiments of the invention feature a smoke detector that includes, consists essentially of, or consists of a housing, one or more light emitters, one or more light detectors, one or more sensors for detecting one or more fire signatures other than smoke, and an evaluation circuit. The one or more light emitters emit, to a sampling volume within and/or outside of the housing, light of a first wavelength and a second wavelength longer than the first wavelength. The light detectors detect light emitted from the one or more light emitters reflected back to the one or more light detectors, thereby providing measurements of reflected light including the first and second wavelengths. The evaluation circuit (i) compares an output of at least one light detector and/or at least one sensor to a threshold and, (ii) if the threshold is exceeded, determines the presence of smoke particles within the sampling volume based on (a) a measurement of reflected light including the first wavelength and (b) a measurement of reflected light including the second wavelength.

Embodiments of the invention may include one or more of the following in any of a variety of combinations. The one or more sensors may include or consist essentially of an ambient light sensor. The evaluation circuit may be configured to (i) correct a measurement of reflected light including the first wavelength based on the detected ambient light level, thereby producing a corrected first-wavelength measurement, (ii) correct a measurement of reflected light including the second wavelength based on the detected ambient light level, thereby producing a corrected second-wavelength measurement, and (iii) determine the presence of smoke particles within the sampling volume based on the corrected first-wavelength measurement and/or the corrected second-wavelength measurement (e.g., a ratio or a difference of the corrected first-wavelength measurement to the corrected second-wavelength measurement). The one or more sensors may include, consist essentially of, or consist of an ambient light sensor, a heat sensor, a humidity sensor, a gas sensor, a proximity sensor, and/or a sound sensor. The sampling volume may be disposed inside and/or outside of the housing. The evaluation circuit may be configured to (i) compare the output of an ambient light sensor to the threshold, and (ii) signal that the threshold is exceeded if the output of the ambient light sensor comprises a characteristic signature of a flicker of a fire. The characteristic signature of the flicker of a fire may have a frequency ranging from approximately 1 Hz to approximately 20 Hz.

These and other objects, along with advantages and features of the invention, will become more apparent through reference to the following description, the accompanying drawings, and the claims. Furthermore, it is to be understood that the features of the various embodiments described herein are not mutually exclusive and can exist in various combinations and permutations. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The term "light" broadly connotes any wavelength or wavelength band in the electromagnetic spectrum, including, without limitation, visible light, ultraviolet radiation, and infrared radiation. Similarly, photometric terms such as "luminance," "luminous flux," and "luminous intensity" extend to and include their radiometric equivalents, such as "radiance," "radiant flux," and "radiant intensity." As used herein, a "portion of light" means an intensity or directional fraction of light that may or may not be discrete from other portions of the same light. As used herein, the term "substantially" means±10%, and in some embodiments, ±5%. The term "consists essentially of" means excluding other materials that contribute to function, unless otherwise defined herein. Nonetheless, such other materials may be present, collectively or individually, in trace amounts.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

Figure 1:
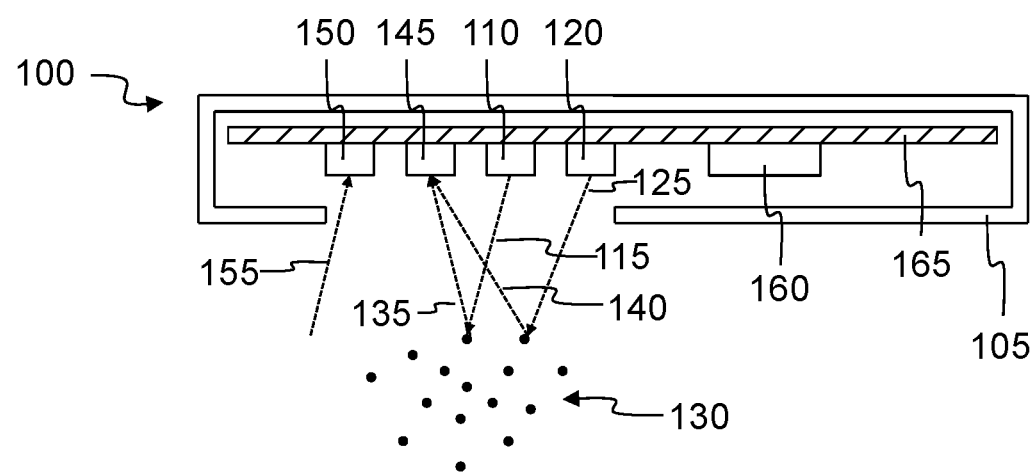
FIG. 1 is a cross-sectional diagram of a smoke detector with an external sampling volume in accordance with various embodiments of the invention.
Figure 3:
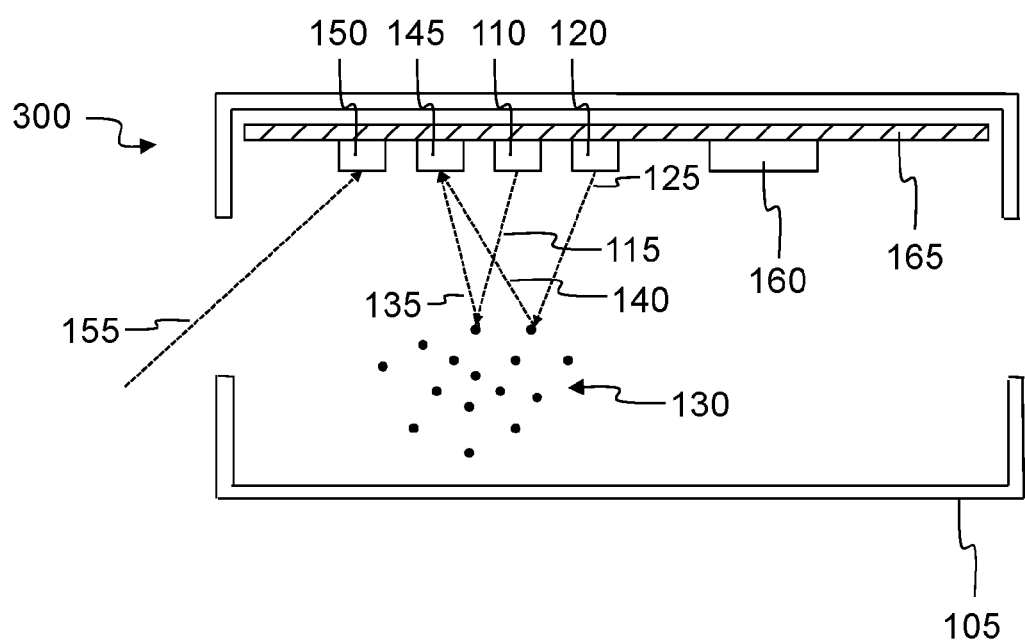
FIG. 3 is a cross-sectional diagram of a smoke detector with an internal sampling volume in accordance with various embodiments of the invention.

An exemplary smoke detector 100 in accordance with embodiments of the present invention is illustrated in FIG. 1. In the exemplary embodiment depicted in FIG. 1, the sampling volume of smoke detector 100 is located predominantly outside a housing 105. As shown, the smoke detector 100 contains a first light emitter 110 emitting a first light beam 115 containing at least a first wavelength and a second light emitter 120 emitting a second light beam 125 containing at least a second wavelength different from the first wavelength. Both light beams 115, 125 are scattered by particles 130 (e.g., smoke particles) located in the sampling volume, resulting in a first scattered beam 135 containing the first wavelength and a second scattered beam 140 containing the second wavelength. The first scattered beam 135 and second scattered beam 140 are collected by a light receiver 145. As utilized herein, a "light receiver" or "light detector" is a discrete or embedded electronic component that registers the presence of and/or measures a property of light (e.g., luminance, wavelength, etc.) when it is illuminated by the light. A light receiver includes or consists essentially of one or more devices that register the presence of and/or measure a property the light illuminating the device(s). For example, the light receiver may produce charge (i.e., an electronic signal) when exposed to light. Exemplary light receivers include photodiodes, photodetectors, photoconductors, and/or photocapacitors. The sampling volume in FIG. 1, i.e., the region outside the smoke detector 100 but within the specified range of the light receiver 145 (or other components described herein) is defined herein as an "external sampling volume." In contrast, FIG. 3 depicts an "internal sampling volume" disposed within the housing of a smoke detector.

The first light emitter 110 and second light emitter 120 may be separate and discrete light emitters, as shown in FIG. 1. In various embodiments, the first wavelength is shorter than the second wavelength. In various embodiments, the first wavelength is ultraviolet or visible (200-700 nm), and the second wavelength is infrared (700-1100 nm). The first light emitter 110 and second light emitter 120 may also be portions of (and/or contained within) a single light emitter emitting multiple wavelengths, such as a white (i.e., broadband) LED. In addition, various embodiments of the present invention utilize multiple light receivers in the smoke detector 100, at least one responsive to the first wavelength and at least one responsive to the second wavelength.

In various embodiments, the smoke detector 100 contains an additional sensor 150 that is responsive to a fire signature 155, other than smoke, which originates from the fire event outside the smoke detector 100. Sensor 150 may include or consist essentially of, but is not limited to, an ambient light sensor (where fire signature 155 is a light beam), a heat sensor (where fire signature 155 is a thermal gradient), a humidity sensor (where fire signature 155 is moisture), a gas sensor (where fire signature 155 is a gaseous combustion byproduct), a proximity sensor (where fire signature 155 is soot and/or another airborne effluent from the fire event), or a sound sensor (where fire signature 155 is a pressure wave).

In embodiments of the invention, the smoke detector 100 may also feature an ambient light sensor in addition to one or more sensors 150, or at least one sensor 150 may include, consist essentially of, or consist of an ambient light sensor.

The ambient light sensor may be a photonic sensor, such as a photodiode or photoconductor, which is responsive to ultraviolet, visible, or infrared light. The ambient light sensor may also be a thermal sensor, such as a thermopile or pyroelectric detector, which is responsive to infrared (thermal) radiation. Ambient light, as utilized herein, is any light that enters the sampling volume and/or the housing that did not originate from a light emitter inside or associated with the smoke detector. Ambient light sensors in accordance with embodiments of the present invention may be responsive to any of a variety of different wavelengths of light, e.g., ultraviolet (200-400 nm), visible (400-700 nm), near infrared (700-1100 nm), short-wavelength infrared (1100-2500 nm), mid-wavelength infrared (2500-7000 nm), and/or long-wavelength infrared (7000-14000 nm). Example ambient light sources include sunlight or light from incandescent, fluorescent, halogen, or LED light bulbs. The gas sensor may be responsive to one or more typical combustion byproducts such as carbon monoxide, carbon dioxide, and/or volatile organic compounds. The proximity sensor type may be optical, capacitive, or ultrasound. The sound sensor may be a microphone or another type of pressure transducer.

In various embodiments, the smoke detector 100 may contain multiple additional sensors. For example, the smoke detector 100 may contain an ambient light sensor, a heat sensor, and a gas sensor. If the smoke detector 100 contains an ambient light sensor, it may also serve as the light receiver 145, so that the functions of ambient light sensing and scattered light sensing are performed by the same component.

The signals produced by the light receiver 145 and sensor 150 are transmitted to an evaluation circuit 160, which may be mounted on a circuit board 165. Evaluation circuit 160 may be a microprocessor, microcontroller, or other programmable circuit. Evaluation circuit 160 processes the signals and determines whether or not a fire event is present. Evaluation circuit 160 may also control the function and timing of the first light emitter 110, second light emitter 120, light receiver 145, and/or sensor 150.

Figure 2:
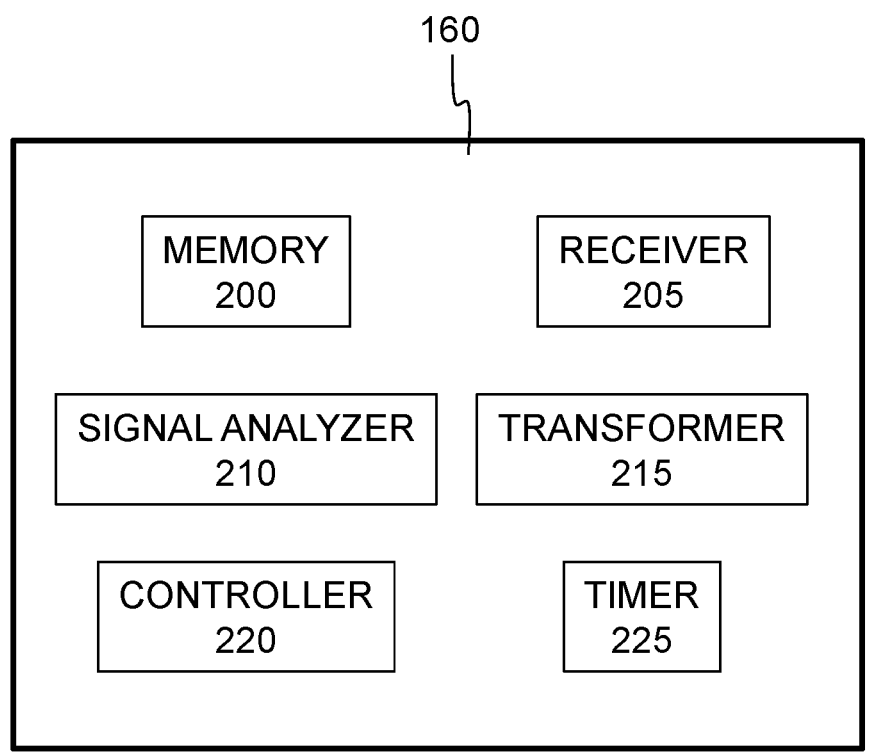
FIG. 2 is a block diagram of an evaluation circuit in accordance with various embodiments of the invention.

FIG. 2 schematically depicts various components of the evaluation circuit 160, which may include (but not be limited to) a memory 200, a receiver 205, a signal analyzer 210, a transformer 215, a controller 220, and/or a timer 225. The memory 200 may store pre-determined values (e.g., thresholds) utilized in sensing and/or control operations, and/or may store various signal values during and/or after they are sensed, corrected, and/or transformed (e.g., smoothed). At least a portion of memory 200 may be volatile, and/or at least a portion of memory 200 may be non-volatile. The receiver 205 may receive signals from other components of the smoke detector (e.g., light detectors and other sensors) and route the signals to other portions of the evaluation circuit 160. The signal analyzer 210 may compare received (and/or corrected and/or transformed) signals to various pre-determined threshold levels and/or to previously received (and/or corrected and/or transformed) signals to determine if smoke particles, other fire signatures, nuisance particles, and/or an obstruction is present. The transformer (or "transform module" or "transformation module") 215 may transform received signals to, e.g., reduce or eliminate noise and/or compensate for drift. For example, the transformer 215 may implement smoothing (e.g., exponential smoothing and/or moving-average smoothing), filtering (e.g., high-pass, low-pass, and/or band-pass filtering), regression, and/or other numerical transformation techniques. The transformer 215 may also correct received signals based on, e.g., other received signals from one or more light detectors and/or sensors (e.g., ambient-light sensors). The controller 220 may control light emitters, light detectors, sensors, and/or other components of the smoke detector; for example, the controller 220 may control speakers that emit audible alarms and/or light sources in response to a sensed alarm condition or as part of a test sequence. The timer 225 may measure time elapsed during or since various sensed conditions and/or may be utilized to measure pre-determined delays utilized in various sensing or testing sequences.

The evaluation circuit 160 (and/or any or all of its components) may be a general-purpose microprocessor, but depending on implementation may alternatively be a microcontroller, peripheral integrated circuit element, a customer-specific integrated circuit (CSIC), an application-specific integrated circuit (ASIC), a logic circuit, a digital signal processor, a programmable logic device such as a field-programmable gate array (FPGA), a programmable logic device (PLD), a programmable logic array (PLA), an RFID processor, smart chip, or any other device or arrangement of devices that is capable of implementing the steps of the processes of embodiments of the invention. In various embodiments, the evaluation circuit 160 is a microcontroller. The evaluation circuit 160 may be monolithically integrated with, and thus a portion of the same integrated-circuit chip as the light receiver 145 and/or the sensor 150, or evaluation circuit 160 may be disposed on a chip separate and discrete from the chip containing the light receiver 145 and/or the sensor 150 (and interconnected thereto by wireless means (e.g., a wireless (e.g., RF) transmitter and receiver) or by one or more wires or other interconnects). Moreover, at least some of the functions of evaluation circuit 160 may be implemented in software and/or as mixed hardware-software modules. Software programs implementing the functionality herein described may be written in any of a number of high level languages such as FORTRAN, PASCAL, JAVA, C, C++, C#, BASIC, various scripting languages, and/or HTML. Additionally, the software may be implemented in an assembly language directed to a microprocessor resident in evaluation circuit 160. The software may be embodied on an article of manufacture including, but not limited to, a floppy disk, a jump drive, a hard disk, an optical disk, a magnetic tape, a PROM, an EPROM, EEPROM, field-programmable gate array, CDROM, or DVDROM. Embodiments using hardware-software modules may be implemented using, for example, one or more FPGA, CPLD, or ASIC processors.

Another exemplary smoke detector 300 in accordance with embodiments of the present invention is illustrated in FIG. 3. In the embodiment depicted in FIG. 3, the sampling volume of smoke detector 300 is located predominantly inside the housing 105. There is at least one opening in housing 105 to allow the entry of smoke particles 130 and fire signature 155. In accordance with various embodiments, the smoke detector 300 may contain an internal chamber (and/or one or more other physical structures such as baffles) substantially blocking ambient light from reaching the first light emitter 110, second light emitter 120, and light receiver 145 while still allowing the entry of smoke particles 130.

Figure 4:
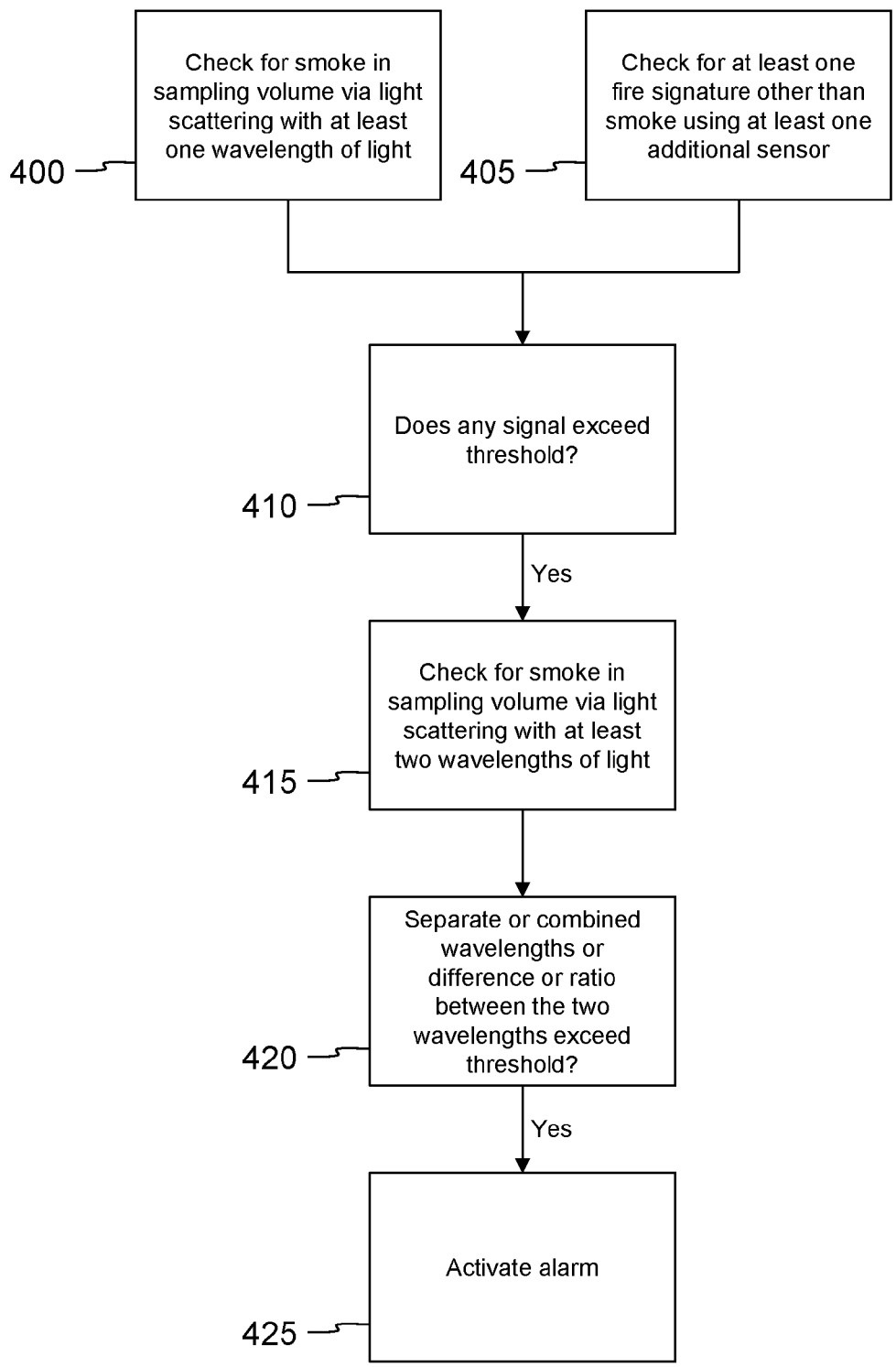
FIG. 4 is a flow chart of a technique of fire-event detection in accordance with various embodiments of the invention.

A technique of fire detection in accordance with various embodiments of the invention is outlined in FIG. 4. In step 400, the presence of smoke in the sampling volume is checked using light scattering with at least one wavelength of light. This wavelength of light may be infrared, because infrared light is invisible to the human eye and infrared LEDs typically operate at a lower voltage than visible or ultraviolet LEDs, consuming less power. The light emitter(s) 110, 120 may operate in pulsed mode to further reduce power consumption.

In step 405, the presence of a fire signature other than smoke is checked using at least one additional sensor 150. The sensor 150 may be responsive to light, heat, humidity, certain gases, proximity, and/or sound, as detailed above. Sensor 150 may be sampled at the same time as light receiver 145, or sensor 150 and light receiver 145 may be sampled sequentially. The signals from sensor 150 and light receiver 145 may be averaged, smoothed, and/or filtered to increase the signal-to-noise ratio.

In step 410, the signals from both sensor 150 and light receiver 145 are compared to pre-determined threshold values. The threshold values may be static or dynamically adjusted based on internal or external environmental conditions. In embodiments in which sensor 150 includes or consists essentially of an ambient light sensor, the sensor 150 may also identify the characteristic flicker of a flaming fire, which typically has a frequency of 1-20 Hz. Identifying the low-frequency flicker may differentiate a flaming fire from sunlight or artificial light, to avoid false positives from the sensor 150. Thus, in various embodiments of the invention in which sensor 150 includes or consists essentially of an ambient light sensor, not all light detected by sensor 150 will be sufficient to signal a fire event (e.g., exceed its threshold); rather, the evaluation circuit 160 may be configured to ignore ambient light lacking the characteristic signature of a flickering fire.

If any signal from sensor 150 and/or light receiver 145 exceeds its threshold, then in step 415 the presence of smoke in the sampling volume is more deeply checked or evaluated using light scattering with at least two wavelengths of light. As described above, the signal from light receiver 145 may be averaged, smoothed, and/or filtered to increase the signal-to-noise ratio. The deeper (or "secondary") check yields a more reliable determination of whether smoke particles or nuisance particles are present in the sampling volume, but it may involve a larger number of measurements and consume more power than the initial check in step 400. It may not be practical to perform the deeper check constantly due to, e.g., excessive power consumption. On the other hand, relying on just the initial check in step 400 may delay the time to activate, because of the time needed for smoke to travel from the fire source to the smoke detector and build up to a sufficient level of obscuration. Therefore, an advantage of techniques in accordance with embodiments of the invention is, by detecting additional fire signatures other than smoke, the delay to perform the deeper check is reduced, and the time to activate if a fire event is present is likewise reduced.

Multiple wavelengths may be emitted by multiple, narrowband light emitters or a single, broadband light emitter. Multiple wavelengths may be received by multiple, narrowband light receivers or a single, broadband light receiver. If multiple light emitters are used, they may be pulsed sequentially or simultaneously. If multiple light receivers are used, they may be sampled sequentially or simultaneously.

If no signal from sensor 150 and/or light receiver 145 exceeds its threshold, then steps 400, 405 may be repeated either continuously or after a delay. The delay between such cycles may be a pre-determined constant value or may change dynamically based on one or more of the comparisons performed in step 410. For example, the delay between cycles may be decreased if any signal from sensor 150 and/or light receiver 145 approaches (e.g., is within 75%, 80%, 85%, or 90% of) its respective threshold. Similarly, the delay between cycles may be increased, and/or reset to a pre-determined default value, if the signals from sensor 150 and/or light receiver 145 are sufficiently low compared to their thresholds (e.g., no greater than 5%, 10%, 15%, or 20% of their thresholds). In this manner, smoke detectors in accordance with embodiments of the invention may query the sampling volume more rapidly as threshold values of various possible signatures of a fire event are approached but may query the sampling volume less often in the absence of such signatures in order to decrease power consumption.

In step 420, the readings from step 415 are compared to one or more pre-determined threshold values. Comparisons may be made to at least one separate (for sequential sampling) or combined (for simultaneous sampling) reading. Comparisons may also be made to a sum, a difference, or a ratio (quotient) of the readings. If two wavelengths of light are used and there are multiple readings collected for each wavelength, then each set of readings may correspond to a point in two-dimensional space. The ratio may be determined by the slope of an imaginary line that is fitted to the points. If any one or more of the readings exceed a threshold value, then in step 425 the alarm is activated. For example, the smoke detector may emit an audible tone or visible light on the smoke detector itself or on an external notification device in wired or wireless communication with the smoke detector.

If none of the readings exceeds its threshold value in step 420, the fire-detection technique may repeat step 415 for one or more cycles, either substantially constantly or with a pre-determined static or dynamic delay between such cycles. As detailed above, any delay between such cycles may be a function of how close any one or more of the readings is to its alarm threshold. Alternatively, or after one or more repeated cycles of step 415, 420 without triggering the alarm, the fire-detection technique may reset back to steps 400, 405, whereupon the entire technique may be repeated.

Figure 5:
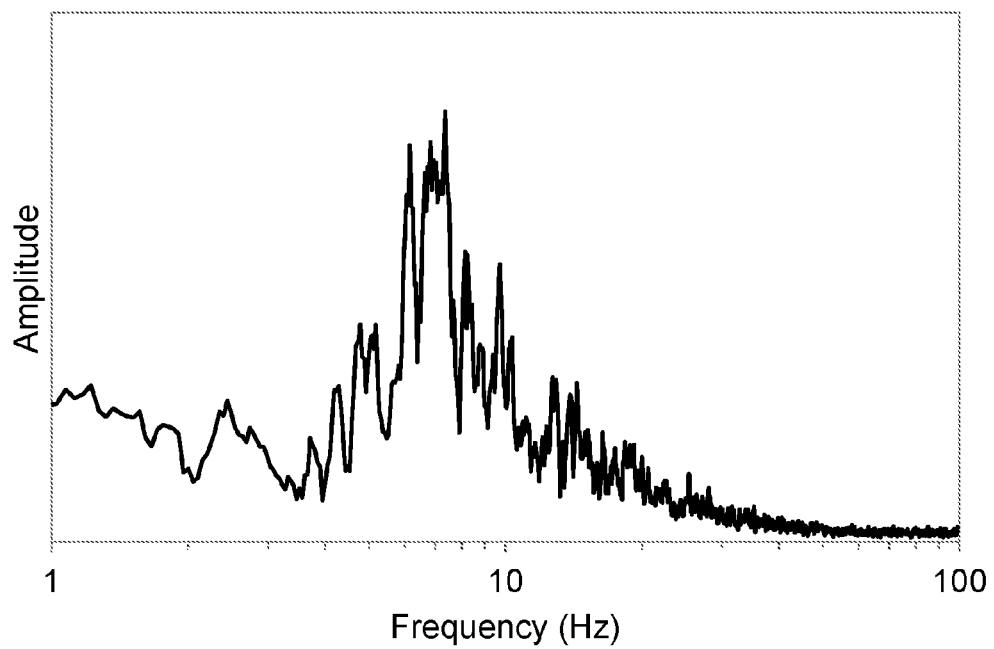
FIG. 5 is a graph of a fast Fourier transform of an exemplary signal generated by an ambient light sensor after ignition of a polyurethane foam fire in accordance with various embodiments of the invention.
Figure 6:
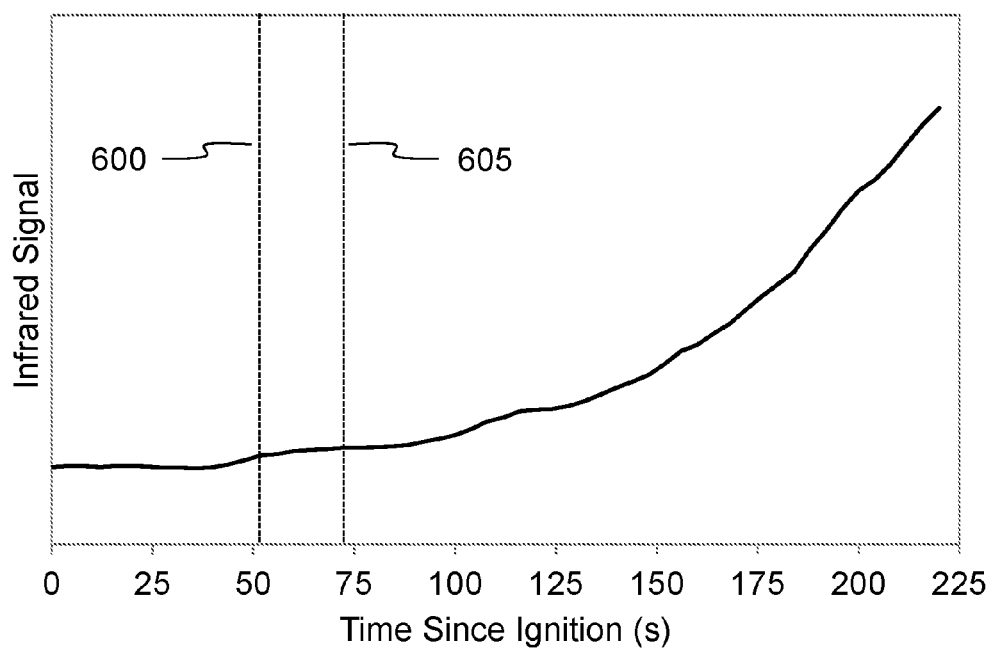
FIG. 6 is a graph of an exemplary scattered-light infrared signal generated by a smoke detector, which closely tracks the smoke obscuration level, in accordance with various embodiments of the invention.

FIGS. 5 and 6 show experimental results from a smoke detector 100, in which sensor 150 included an ambient light sensor, and utilizing the technique in FIG. 4. The smoke detector was placed approximately 17 feet away from a flaming polyurethane foam fire. After ignition of the polyurethane foam, flames and smoke were generated at the fuel source in less than 10 seconds, but it took approximately 44 seconds for the smoke to travel the full length to the smoke detector.

A fast Fourier transform (FFT) of the signal generated by the ambient light sensor after ignition of the polyurethane foam is plotted in FIG. 5. There is a large peak at a frequency of approximately 7 Hz, which is characteristic of the flicker of a flaming fire. The peak may be differentiated from sunlight, which essentially has no flicker, and artificial light, which has a flicker of approximately 100 Hz and/or 120 Hz.

The infrared signal generated by the smoke detector, which closely tracks the smoke obscuration level, is plotted in FIG. 6. As stated above, smoke first reached the smoke detector approximately 44 seconds after ignition, visible as a slight increase in the infrared signal. There are two activation times plotted in FIG. 6, corresponding to which sensor triggered the deeper check for the presence of smoke.

When the ambient light sensor was used to trigger the deeper check, an activation time 600 was approximately 52 seconds after ignition. When the ambient light sensor was ignored, and instead the infrared signal alone triggered the deeper check, an activation time 605 was approximately 72 seconds after ignition. Thus, by incorporating an additional sensor in the smoke detector to initiate the deeper check earlier, the activation time for detection of the flaming polyurethane foam fire was reduced by 20 seconds.

Figure 7:
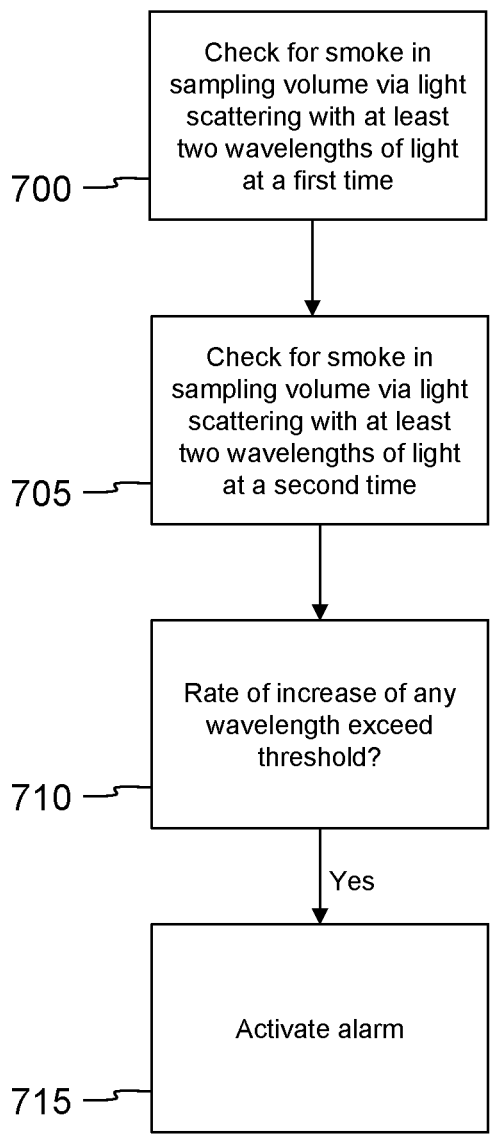
FIG. 7 is a flow chart of a technique of fire-event detection in accordance with various embodiments of the invention.

Another exemplary fire-detection technique in accordance with various embodiments of the invention is outlined in FIG. 7. In step 700, the presence of smoke in the sampling volume is checked using light scattering with at least two wavelengths of light at a first time. In step 705, the presence of smoke in the sampling volume is checked using light scattering with at least two wavelengths of light at a second time later than the first time. Multiple wavelengths may be emitted by multiple, narrowband light emitters or a single, broadband light emitter. Multiple wavelengths may be received by multiple, narrowband light receivers or a single, broadband light receiver. If multiple light emitters are used, they may be pulsed sequentially or simultaneously. If multiple light receivers are used, they may be sampled sequentially or simultaneously. At each time, multiple signals may be taken and averaged, smoothed, and/or filtered to increase the signal-to-noise ratio. The timing of and/or between the measurements may be kept by, e.g., timer 225 or another timing circuit elsewhere within the smoke detector.

In step 710, the rate of increase of the signal corresponding to at least one wavelength is determined and compared to a pre-determined threshold value. The rate of increase may be determined by dividing the change in the readings taken at the first and second times by the change in time. Fires, especially flaming fires, generally build up to a given level of obscuration more quickly than nuisance sources. If the rate of increase determined in step 710 exceeds the threshold value, then in step 715 the alarm is activated. For example, the smoke detector may emit an audible tone or visible light on the smoke detector itself or on an external notification device in wired or wireless communication with the smoke detector.

If no signal exceeds its threshold in step 710, then steps 700, 705 may be repeated either continuously or after a delay. The delay between such cycles may be a pre-determined constant value or may change dynamically based on one or more of the comparisons performed in step 710. For example, the delay between cycles may be altered as a function of the difference between the detected signal and its threshold, as detailed above with reference to FIG. 4. In this manner, smoke detectors in accordance with embodiments of the invention may query the sampling volume more rapidly as threshold values are approached but may query the sampling volume less often in the absence of signals approaching threshold values in order to decrease power consumption.

Embodiments of the present invention may be combined with, and/or otherwise utilized with, systems and techniques described in U.S. patent application Ser. No. 13/799,816, filed Mar. 13, 2013, Ser. No. 13/799,826, filed Mar. 13, 2013, Ser. No. 13/800,071, filed Mar. 13, 2013, Ser. No. 14/067,431, filed Oct. 30, 2013, and/or Ser. No. 14/522,971, filed Oct. 24, 2014, the entire disclosure of each of which is incorporated by reference herein.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A method of smoke detection utilizing a smoke detector comprising (a) a housing, (b) one or more light emitters, and (c) one or more light detectors, the method comprising:
   during a first time period, (i) acquiring, from a sampling volume, a first measurement of light including a first wavelength while emitting light of approximately the first wavelength into the sampling volume with at least one said light emitter, and (ii) acquiring, from the sampling volume, a second measurement of light including a second wavelength longer than the first wavelength while emitting light of approximately the second wavelength into the sampling volume with at least one said light emitter;
   during a second time period later than the first time period by an elapsed time, (i) acquiring, from the sampling volume, a third measurement of light including the first wavelength while emitting light of approximately the first wavelength into the sampling volume with at least one said light emitter, and (ii) acquiring, from the sampling volume, a fourth measurement of light including the second wavelength while emitting light of approximately the second wavelength into the sampling volume with at least one said light emitter; and
   determining the presence of smoke particles within the sampling volume based on at least one of (i) a rate of change between the first and third measurements, or (ii) a rate of change between the second and fourth measurements.

2. The method of claim 1, wherein determining the presence of smoke particles within the sampling volume comprises at least one of (i) comparing to a threshold a difference between the first and third measurements divided by the elapsed time, or (ii) comparing to a threshold a difference between the second and fourth measurements divided by the elapsed time.

3. The method of claim 1, wherein at least a portion of the second measurement is acquired while emitting light of approximately the first wavelength with at least one said light emitter.

4. The method of claim 1, wherein at least a portion of the first measurement is acquired while emitting light of approximately the second wavelength with at least one said light emitter.

5. The method of claim 1, wherein at least a portion of the fourth measurement is acquired while emitting light of approximately the first wavelength with at least one said light emitter.

6. The method of claim 1, wherein at least a portion of the third measurement is acquired while emitting light of approximately the second wavelength with at least one said light emitter.

7. The method of claim 1, wherein the sampling volume is disposed outside of the housing.

8. The method of claim 1, wherein the sampling volume is disposed within the housing.

9. The method of claim 1, wherein the presence of smoke particles within the sampling volume is determined based on both (i) the rate of change between the first and third measurements, and (ii) the rate of change between the second and fourth measurements.

10. A method of smoke detection utilizing a smoke detector comprising (a) a housing, (b) one or more light emitters, and (c) one or more light detectors, the method comprising:
   during a first time period, acquiring, from a sampling volume, a first measurement of light including (i) a first wavelength and (ii) a second wavelength longer than the first wavelength while emitting light of approximately the first and second wavelengths into the sampling volume with at least one said light emitter;

during a second time period later than the first time period by an elapsed time, acquiring, from the sampling volume, a second measurement of light including the first and second wavelengths while emitting light of approximately the first and second wavelengths into the sampling volume with at least one said light emitter; and determining the presence of smoke particles within the sampling volume based on a rate of change between the first and second measurements.

11. The method of claim 10, wherein determining the presence of smoke particles within the sampling volume comprises comparing to a threshold a difference between the first and second measurements divided by the elapsed time.

12. The method of claim 10, wherein the sampling volume is disposed outside of the housing.

13. The method of claim 10, wherein the sampling volume is disposed within the housing.

\* \* \* \* \*